United States Patent [19]
Bod et al.

[11] Patent Number: 5,128,477
[45] Date of Patent: Jul. 7, 1992

[54] PROCESS FOR THE PREPARATION OF MORPHOLOGICALLY HOMOGENEOUS FORMS OF THIAZOLE DERIVATIVES

[75] Inventors: Péter Bod, Gyömro; Kálmán Harsányi, Budapest; Béla Hegedüs, Budapest; Erik Bogsch, Budapest; Éva Fekecs, Budapest; Imre Péter, Budapest; Zsuzsanna Aracs née Trischler, Budapest; Sándor Miszori, Budapest; Mária Stiller, Budapest, all of Hungary

[73] Assignee: Richter Gedeon Vegyeszeti Gyar Rt., Budapest, Hungary

[21] Appl. No.: 728,805

[22] Filed: Jul. 11, 1991

Related U.S. Application Data

[60] Continuation of Ser. No. 398,181, Aug. 24, 1989, abandoned, which is a division of Ser. No. 81,423, Aug. 4, 1987, Pat. No. 4,894,459.

[30] Foreign Application Priority Data

Aug. 5, 1986 [HU] Hungary ............................. 3370/86

[51] Int. Cl.$^5$ .......................................... C07D 277/48
[52] U.S. Cl. .................................................... 548/197
[58] Field of Search ........................................ 548/197

[56] References Cited

U.S. PATENT DOCUMENTS 5,021,582  6/1991  Ballester-Roder .................. 548/197

FOREIGN PATENT DOCUMENTS 0128736 12/1984  European Pat. Off. .
0297019 12/1988  European Pat. Off. .
3644246 12/1987  Fed. Rep. of Germany ...... 548/197
2180237  3/1987  United Kingdom ................ 548/197

*Primary Examiner*—Robert Gerstl
*Attorney, Agent, or Firm*—Herbert Dubno; Jonathan Myers

[57] ABSTRACT

The invention relates to two morphologically homogeneous forms of Famotidine [chemical name: N-sulfamoyl-3-(2-guanidino-thiazole-4-yl-methylthio)-propionamidine]. Said forms are prepared by selective crystallization or precipitation.

1 Claim, No Drawings

PROCESS FOR THE PREPARATION OF MORPHOLOGICALLY HOMOGENEOUS FORMS OF THIAZOLE DERIVATIVES

This is a continuation of co-pending application Ser. No. 07/398,181* filed on Aug. 24, 1989, now abandoned which is a division of Ser. No. 07/081,423 filed Aug. 4, 1989, now U.S. Pat. No. 4,894,959.

The invention relates to a process for the preparation of morphologically homogeneous Famotidine.

It is well known that Famotidine [chemical name: N-sulfamoyl-3-(2-guanidino-thiazole-4-yl-methylthio)-propionamidine], whose name according to Chemical Abstracts is 3-(((((2-diamino-methylene)amino)-4-thiazolyl)methyl(thio)-sulfamoylpropionamidine, has an excellent histamine-$H_2$ receptor blocking effect. There is, however, no hint in the literature whether Famotidine has polymorphous forms or not.

During our tests of the hitherto known preparation processes of Famotidine, when analyzing the products of these tests by DSC (differential scanning calorimetry) it has been determined that Famotidine has two forms, i.e. forms "A" and "B". The place of endotherma maximum of these forms, determined by using a heating-rate of 1° C./min., was in the case of form "A" at 167° C. and in the case of form "B" at 159° C.

One of our further observations was that the products of parallel experiments were regularly rather different from each other, especially from the point of view of bulk density and adhesiveness, and rather there were great differences in their infra-red spectra. During experiments performed in an usual way the characteristics of the products changed in a wide range, at random. This statement is supported by the Spanish patent specification No. 536,803 (INKE Co.) with its infrared spectroscopic data, in which the absorption bands 3500, 3400 and 1600 cm$^{-1}$, according to our measurements, unambiguously correspond to form "B" of lower melting point and the band at 3240 cm$^{-1}$ corresponds to form "A" of higher melting point. The mixture-character is proved also by the absorption band at 1000 cm$^{-1}$, which may originate from the fusion of the 1005 and 986 cm$^{-1}$ bands of form "A" and of the 1009 and 982 cm$^{-1}$ bands of form "B". The mixture-character can also be proved if one compares our DSC-data, mentioned in the introduction, with the melting-point data (162°-164° C.) in the above-mentioned Spanish patent specification, as well as with the melting point of 158°-164° C., published in the European patent specification No. 128,736. Thus, it seems to be obvious that in both cases the researchers were in the possession of a mixture of forms "A" and "B" with a non-defined composition.

In the field of pharmaceutical drug production very often the manufacturers do not pay great attention to morphology, because in decisive majority of cases holds the assumption that the identity of structural formula means also the identity of different forms from pharmaceutical point of view. This holds, for example, for most steroid compounds. However, in certain cases there are surprising differences in the bioavailabilies of different forms, as for example in the case of mebendasole [Janssen Pharmaceutica: Clin. Res. Reports No. R 17635/36 (1973)], or extreme differences can be detected in respect of other parameters. Famotidine is one of the best typical representative of this latter case.

The aim of our research work was to clear up the reasons of the different characteristics of Famotidine samples, and furthermore to work out a process for the preparation of different forms of Famotidine with appropriate morphological purity.

In our first research phase we studied the relationship between the morphological properties of products obtained by crystallization when using the most common solvents for pharmaceutical drug manufacturing, taking the solubility properties of Famotidine into account. We could not find such a solvent which would provide one of the forms in all circumstances, but we could observe that in the presence of organic solvents the production of the form "B" of lower melting point was usually hindered.

After these we studied the effect of kinetic conditions of crystallization, and found surprisingly that this is the very parameter which definitively determines the morphological properties of the product obtained.

Studying the relationship between the morphological properties of Famotidine obtained and the kinetic conditions of preparation we found, that for the production of form "A" is most favorable if the crystallization is carried out by starting from a hot solution and using a rather slew cooling rate. In contrast to this, if we obtain the product during crystallization by precipitation caused by rapid over-saturation, the product proves to be characteristically form "B" of lower melting point.

The rapid oversaturation can be achieved by very fast cooling of the Famotidine solution or by quick deliberation of Famotidine base from its salt.

In the case of fast cooling, when using higher volumes one should consider as an uncertainty factor that the velocity of formation of the crystal-nucleus of forms "A" and "B" depends on the chemical purity of the starting materials.

As to the other possibility for accomplishing rapid oversaturation, i.e. deliberation of the Famotidine base from its salt, one has to be very careful, since in a medium with a pH lower than 3 the amidino group is highly capable of hydrolysis. We have found that the salt formation with carboxylic acids, especially with acetic acid, is the most favorable, and the free bases from this salt can be deliberated with ammonium hydroxide, using the reverse dosage method.

Thus, the invention relates, on the one hand, to the form "A" of Famotidine. This form is characterized by that its endotherma maximum of melting is at 167° C. on the DSC; its characteristic absorption bands in its infra-red spectrum are at 3450, 1670, 1138 and 611 cm$^{-1}$, and its melting point is 167°-170° C.

The invention relates, on the other hand, to the form "B" of Famotidine. This form is characterized by its endoterma maximum of melting which is at 159° C. on the DSC; its characteristic absorption bands in its infra-red spectrum are at 3506, 3103 and 777 cm$^{-1}$, and its melting point is 159°-162° C.

The present invention further relates to a process for the preparation of morphologically homogeneous Famotidine. This process is characterized by dissolving Famotidine of optional morphological composition in water and/or a lower aliphatic alcohol under heating and a) in the case of the preparation of the form "A" the hot-saturated solution is crystallized by using a cooling rate of about 1° C./min. or less, b) in the case of the preparation of the form "B" the product is precipitated from its oversaturated solution which was oversaturated at a temperature lower than 40° C., and in both cases the product is separated from the obtained suspension of crystals.

Alcohols of 1-8 carbon atoms are considered as lower alcohols. They can have linear or branched carbon chain and 0, 1 or 2 double bonds, e.g. methanol, ethanol, isopropanol, crotylalcohol etc.

According to an advantageous embodiment of the invention the oversaturated solution is obtained by either cooling a hot solution with a cooling rate greater than 10° C./min. or by deliberating the free basic form of Famotidine from its salt.

The separation by filtration of the products obtained by the process of the invention is carried out at a temperature between −10° C. and +40° C.; the most advantageous temperature is 10°-20° C.

One can also proceed so that the salt of Famotidine formed with acetic acid is added into ammonium hydroxide in order to obtain the free basic form.

The required high cooling rate can be reached by the addition of ice or dry-ice.

It is rather advantageous to add seeding crystals of the required form to the system, before the crystallisation starts.

Form "A" of Famotidine prepared by the process of the invention has an endotherma maximum of melting (on the DSC-curve) with a value of 167° C.; typical absorption bands of its IR-spectrum are at 3450, 1670, 1138 and 611 cm$^{-1}$.

Form "B" of Famotidine prepared by the process of the invention has an endotherma maximum of melting (on the DSC-curve) with a value of 159° C.; typical absorption bands of its IR-spectrum are at 3506, 3103 and 777 cm$^{-1}$.

The greatest advantage of the process of the invention resides in that it gives an easy, well controlled tehnology for the preparation of different forms of Famotidine with a morphological purity of 100% and exactly differenciates the Famotidine polymorphs from each other, as well as from polymorphous mixtures of undefined composition. To demonstrate the importance of describing homogeneous polymorphs instead of polymorphous mixtures a Table is presented from measured data of the pure forms "A" and "B" of Famotidine. All these data correspond to samples taken from industrial scale manufacturing procedures described in Examples I/5 and II/5.

TABLE I

| (A) Infrared spectrum data: | |
|---|---|
| Form "A" | Form "B" |
| 3452, 3408, 3240, 1670, 1647, 1549, 1138, 1005, 984, 906, 611 and 546 cm$^{-1}$ | 3506, 3400, 3337, 3103, 1637, 1533, 1286, 1149, 1009, 982, 852, 777, 638 and 544 cm$^{-1}$ |

(B) DSC MEASUREMENT DATA

The mesurements were performed on a Perkin-Elmer instrument under N$_2$ atmosphere. From the DSC curves taken with pre-defined heating rate, the following data were determined: place of the maximum, the point of intersection of the tangent drawn to the inflexion point of the raising side of the curve and the baseline, the "onset", and the enthalpy value of melting, calculated from the area under the curve. The dimension of the data in columns "Max." and "Onset" is °C. and in the column "enthalpy" is J/g.

| Heating rate | Form "A" | | | Form "B" | | |
|---|---|---|---|---|---|---|
| | Max. | Onset | Enthalpy | Max. | Onset | Enthalpy |
| 10° C./min | 172.7 | 171.0 | 159.2 | 164.3 | 162.1 | 149.4 |
| 5° C./min | 172.2 | 170.8 | 159.0 | 163.5 | 161.9 | 147.9 |
| 1° C./min | 166.6 | 165.4 | 138.6 | 158.7 | 157.5 | 138.1 |
| ½° C./min | 164.3 | 163.3 | 132.9 | 165.2 | 154.9 | 130.1 |
| ¼° C./min | 160.3 | 159.6 | 113.1 | 152.8 | 152.0 | 128.9 |

(C) X-RAY DIFFRACTION DATA:

The data shown here were measured on a Philips instrument, and indicate layer-distances; their dimension is Å.

| Form "A" | Form "B" |
|---|---|
| 8.23, 6.29 5.13, 4.78, 4.44, 4.30 (basis), 4.24, 3.79, 3.43, 2.790 and 2.675 | 14.03, 7.47, 5.79, 5.52, 4.85, 4.38, 3.66 (basis), 2.95 and 2.755 |

(D) BULK DENSITY

| | Form "A" | Form "B" |
|---|---|---|
| Without compaction | 695 g/l | 340 g/l |
| With compaction | 960 g/l | 505 g/l |
| Compaction ratio | 1.38 | 1.47 |

The compaction was made with a hand-vibrator for 5 minutes.

(E) ADHESIVENESS AND ARCHING/CAVING TENDENCY

| Form "A" | Form "B" |
|---|---|
| does not arch powder-like | heavily arching agglutinates into nodes |

(F) ROLLING ANGLE DATA

The data given here were measured according to the following scheme:

The form to be tested was filled into a funnel provided with a tube of 5 mm diameter, then the funnel was set into a position so that its opening was 10 cm above the level of the material. The basic angles of the cones formed from the grains flowing through are given below.

| Form "A" | Form "B" |
|---|---|
| 41-42° | more than 55°[x] |

[x]In the case of form '37 B" we were not able to measure the correct data for rolling angle, because at the beginning the sample piled up with 80-85° slope and then 1-2 mm coagulates lose the wall. The given data correspond to this observation.

THE DEFORMITY RATIO OF THE CRYSTALS

Deformity ratio means the ratio of the longitudinal axis and greatest diameter of the crystal.

The data were determined from the measurement of 250-250 grains by averaging.

| Form "A" | Form "B" |
|---|---|
| 1.40 | 4.70 |

(H) SOLUBILITY DATA

Saturation solubility

The investigation was made as follows: the different forms were stirred in distilled water for 5 hours, and the concentration of the material in solution was determined by ultraviolet spectroscopy at 277 nm wavelength.

| Form "A" | Form "B" |
|---|---|
| 860 mg/l | 980 mg/l |

Dynamic solubility

The investigation was made as follows: 10-10 mg of the form to be tested were weighed into 100 ml of distilled water, under stirring. At appropriate times samples were taken from the system, and after filtration and appropriate dilution the amount of dissolved Famotidine was determined by ultraviolet spectrophotometry.

| Time | Form "A" | Form "B" |
|---|---|---|
| 2 min | 19 mg/l | 25 mg/l |
| 5 min | 25 mg/l | 40 mg/l |
| 10 min | 42 mg/l | 51 mg/l |
| 1 hour | 72 mg/l | 76 mg/l |

(I) THERMODYNAMIC STABILITY

The test was made as follows: a mixture of the different forms in a ratio of 95:5 for both derivatives contaminated with the other polymorph was prepared, then the system was stirred with a magnetic stirrer for 24 hours at 60° C. so that water only covered the crystals. The crystals were then filtered and morphologically studied. In both bases the product proved to be form "A".

| Form "A" | Form "B" |
|---|---|
| stabile | metastabile |

Concerning the above observations one has to consider the form with a higher melting-point as form "A".

(J) ELECTROSTATIC CHARGING

As there is no simple procedure to be carried out in an organic chemistry laboratory, the data presented below were measured as follows:

Into a glass dish of 120 mm diameter 37 g of one of the forms were transferred and then the sample was stirred for 1 minute with rubbing with a flattened end glass-rod. Following this, the content of the dish was poured out without shaking, and the amount of stuck material was measured on a balance. Then the measurement was repeated so that the dish was knocked 10 times.

| | Form "A" | Form "B" |
|---|---|---|
| Without knocking | 2.8 g | 13 g |

-continued

| | Form "A" | Form "B" |
|---|---|---|
| After knocking | 0.5 g | 10.0 g |

The data of the above Table clearly point to the significance of the present invention, but the results at several properties are worth discussion.

(1) In the region of the infrared spectrum that is best evaluatable, above 3500 cm$^{-1}$, only the form "B" has an absorption band. It is such a characteristics one that it makes possible even with a spectrophotometer of traditional optical arrangement to detect the presence of 5% of form "B" in form "A" of Famotidine.

(2) There is roughly a twofold difference in the bulk density data, which means that in the case of material with undefined morphology, measuring with by the aid of a graduated cylinder would give a possibility of significant errors.

(3) There is a difference of an order of magnitude in the electrostatic charging tendency of the two forms. The amount of the strongly attracted form "B" is 20 times more than the amount of form "A".

(4) Concerning the rolling and arching tendency data, the characteristic data differ not only in values, but also in sign. Only for one or for the other specific morphologic form alone is it possible to develop a package technology which is reliable; it is impossible for morphological mixtures of unreproducible composition.

(5) The deformity ratio-values, defined for the description of the shape of crystals, show indirectly the specific surface, respectively they show how much it is possible that the crystals will stick together, i.e. they reflect adhesiveness and nodule formation. These values are 3.3 times higher in the case of form "B" than in the case of form "A".

(6) Because of the higher specific surface, mentioned above, the dissolving velocity of form "B" is considerably higher than that of form "A". Concerning the saturating solubility data, the value for form "B" is also significantly higher.

Since Famotidine was not yet published in the pharmacopoeia, it is impossible for the time being to give a clear-cut answer which of the two forms described in this application has a better therapeutical value. From the point of view of handling and stability the properties of form "A" are unambiguously more advantageous, but one should not forget that in the case of pharmaceutical products the dissolving rate is of crutial importance, and this latter is higher in the case of form "B".

The invention is elucidated in detail by the aid of the following non-limiting Examples. Examples of group I relate to the production of form "A", and Examples of group II relate to preparation of form "B".

EXAMPLE I/1

10 g of Famotidine of optional morphological composition (hereinafter called simply Famotidine) are dissolved in 100 ml of water by quick boiling. The solution is allowed to cool from 100° C. to 20° C. within 3 hours. Following a 30 minutes stirring at 15°-20° C., the precipitated crystalline product, appearing in monoclinal prismatic form, is filtered and dried. Yield: 9.4 g (94%). M.p.: 167°-169° C. Further physical-chemical parameters of the product: DSC: 167° C. [at 1° C./min heating-rate]. The most characteristic infrared absorption bands: 3452, 3408, 3240, 1670, 1647, 1549, 1138, 1005, 984, 906, 611 and 546 cm$^{-1}$. Powder X-ray diffraction data: (layer-distances in Å): 8.23, 6.09, 5.13,, 4.78, 4.44, 4.30 (basis), 4.24, 3.79, 3.43, 2.790 and 2.675.

EXAMPLE I/2

10 g of Famotidine are dissolved in 70 ml of 50% aqueous methanol by boiling, under stirring. The solution of 78° C. is clarified, filtered and cooled to room temperature within 3 hours. This is followed by a 30 minutes stirring. This way 8.4 g of microcrystalline form "A" with a melting point of 167°–169° C. are obtained. The further physical parameters are the same as given in example I/1.

EXAMPLE I/3

10 g of Famotidine are dissolved hot in 50 ml of 50% aqueous ethanol under stirring. The solution is allowed to cool to room temperature within 3 hours and then stirred again for one hour. After filtration and drying 9.5 g (95%) of form "A" with a melting point of 167°–169° C. are obtained. The further physical parameters are the same as given in example I/1.

EXAMPLE I/4

10 g of Famotidine are dissolved in 60 ml of 50% aqueous isopropanol with quick boiling. The solution is allowed to cool uniformly within 3 hours. The resulting crystals are filtered and dried.
Weight of product: 9.4 g (94%)
M.p.: 167°–169° C.
The further physical parameters are the same as given in example I/1.

EXAMPLE I/5

In a 1000 liter volume apparatus, under boiling and stirring a solution is made from 70 kg of Famotidine, 427.5 kg of deionized water and 124 kg (157.5 l) of ethanol. The resulted solution of 80° C. is cooled slowly, within 5–6 hours, to 20° C. under continuous stirring. After stirring at 15°–20° C. for one hour followed by centrifuging and drying, 67 kg of form "A" with a melting point of 167°–170° C. are obtained. The further physical parameters are the same as given in example I/1.

EXAMPLE II/1

10 g of Famotidine of optional morphological composition (hereinafter called Famotidine) are dissolved with quick boiling in water under stirring. Immediately after dissolving, the solution is started to be cooled with an ice bath, under continuous stirring. Form "B", appearing in needle-shaped crystal form, is filtered and dried. The weight of the product is 9.4 g (94%), its melting point is 159°–161° C. Further physico-chemical parameters of the product:
DSC: 159° C. [at 1° C./minute heating-rate]
The most characteristic infrared absorption bands: 3506, 3400, 3337, 3103, 1637, 1533, 1286, 1149, 1009, 982, 852, 777, 638 and 544 cm$^{-1}$.

Powder X-ray diffraction data: (layer-distances in Å): 14.03, 7.47, 5.79, 5.52, 4.85, 4.38, 4.13, 3.66 (basis), 2.954, 2.755.

EXAMPLE II/2

5 g of Famotidine are dissolved in 40 ml of 75% aqueous methanol with quick boiling, under continuous stirring. The hot solution is filtered, and the solution is poured under stirring onto ice. This is followed by a one hour after-stirring, form "B", appearing in needle-shaped crystal form, is removed by filtering from the solution. Its weight is 4.55 g (91%), and has a melting point of 159°–161° C. The further physical parameters of the product are the same, as given in example II/1.

EXAMPLE II/3

5 g of Famotidine are dissolved in 30 ml of 50% aqueous isopropanol with short boiling. Then we cool the solution quickly with icy water and after 1 hour stirring the resulted form "B" crystals are separated. The weight of the product after drying is 4.6 g (92%) and has a melting point of 156°–162° C. The further physical parameters are the same as given in example II/1.

EXAMPLE II/4

16.87 g of Famotidine are dissolved in a mixture of 125 ml water and 6.0 g glacial acetic acid with a few minutes stirring. The resulting solution is poured onto a dropping funnel, and dropped into a stirred mixture of 10 ml (25%) ammonia and 20 ml water, with constant rate, at 20°–25° C. temperature. Following the 10 minutes after-stirring, the product is filtered, washed with water and dried. We get 15.8 g form "B" (93.7%), with a melting point of 159°–162° C. The further physical parameters are the same, as given in example II/1.

EXAMPLE II/5

110 kg of Famotidine are dissolved in a mixture of 816 kg deionized water and 39.2 kg glacial acetic acid. The obtained filtered solution is sucked into a dropping-reservoir, and than we load 120 kg deionized water and 60 kg 25% ammonia into a 2000 liter volume apparatus, supplied with a stirrer. Following this we add 550 g seeding crystals of form "B" to the water containing ammonium hydroxide solution and than we feed the Famotidine-acetate solution with constant rate into the apparatus, at 15°–25° C., under stirring within 1–1.5 hours. Following the 30 minutes after-stirring, centrifugating, washing and drying is obtained 99.4 kg (90.4%) form "B". Melting point: 159°–162° C. The further physical parameters are the same, as given in example II/1.

What we claim is:
1. A form "A" of Famotidine characterized by that its endothermal maximum of melting is at 167° C. on the DSC; its characteristic absorption bands in its infrared spectrum are at 3450, 1670, 1138 and 611 cm$^{-1}$, and its melting point is 167°–170° C.

* * * * *